United States Patent
Stylios

(10) Patent No.: US 6,668,231 B2
(45) Date of Patent: Dec. 23, 2003

(54) SHEET PARAMETER MEASUREMENT

(76) Inventor: George Stylios, 42 Sandhill Crescent, Leeds, LS17 8FZ (GB)

(*) Notice: Subject to any disclaimer, the term of this patent is extended or adjusted under 35 U.S.C. 154(b) by 0 days.

(21) Appl. No.: 09/834,076

(22) Filed: Apr. 12, 2001

(65) Prior Publication Data

US 2003/0083828 A1 May 1, 2003

(51) Int. Cl.[7] .................................................. G01L 1/00
(52) U.S. Cl. ........................... 702/43; 73/597; 73/826; 73/833; 162/198; 204/298.03; 250/559.01; 348/128; 356/430; 356/606
(58) Field of Search ............................ 702/38–39, 42, 702/43; 73/788, 826, 833, 841; 250/559.01; 162/198

(56) References Cited

U.S. PATENT DOCUMENTS

| | | | |
|---|---|---|---|
| 4,543,602 A | 9/1985 | Kai et al. | 348/128 |
| 4,674,332 A * | 6/1987 | Pace et al. | 73/597 |
| 4,741,621 A | 5/1988 | Taft et al. | 356/606 |
| 4,900,153 A | 2/1990 | Weber et al. | 356/430 |
| 5,104,488 A * | 4/1992 | Chase | 162/198 |
| 5,122,672 A | 6/1992 | Mansour | 250/559.01 |
| 5,231,882 A | 8/1993 | Bertele et al. | 73/852 |
| 5,703,688 A | 12/1997 | Bell | 356/430 |
| 5,911,166 A * | 6/1999 | Cowan | 73/833 |
| 6,086,734 A * | 7/2000 | Harada | 204/298.03 |
| 6,370,962 B1 * | 4/2002 | Sullivan et al. | 73/826 |

FOREIGN PATENT DOCUMENTS

| | | |
|---|---|---|
| GB | 1377607 | 11/1970 |
| GB | 2171511 A | 8/1986 |
| GB | 2180929 A | 4/1987 |
| JP | 360039531 * | 3/1985 |

* cited by examiner

Primary Examiner—John Barlow
Assistant Examiner—John Le
(74) Attorney, Agent, or Firm—Wallenstein Wagner & Rockey, Ltd.

(57) ABSTRACT

A measuring device useful for measuring mechanical properties of highly flexible or limp sheet materials. The device includes a base, a pair of clamping members, with one of the clamping members being movable away from and toward the second clamping member. A load sensor is mounted in one of the clamping means for measurement of the required mechanical properties.

26 Claims, 2 Drawing Sheets

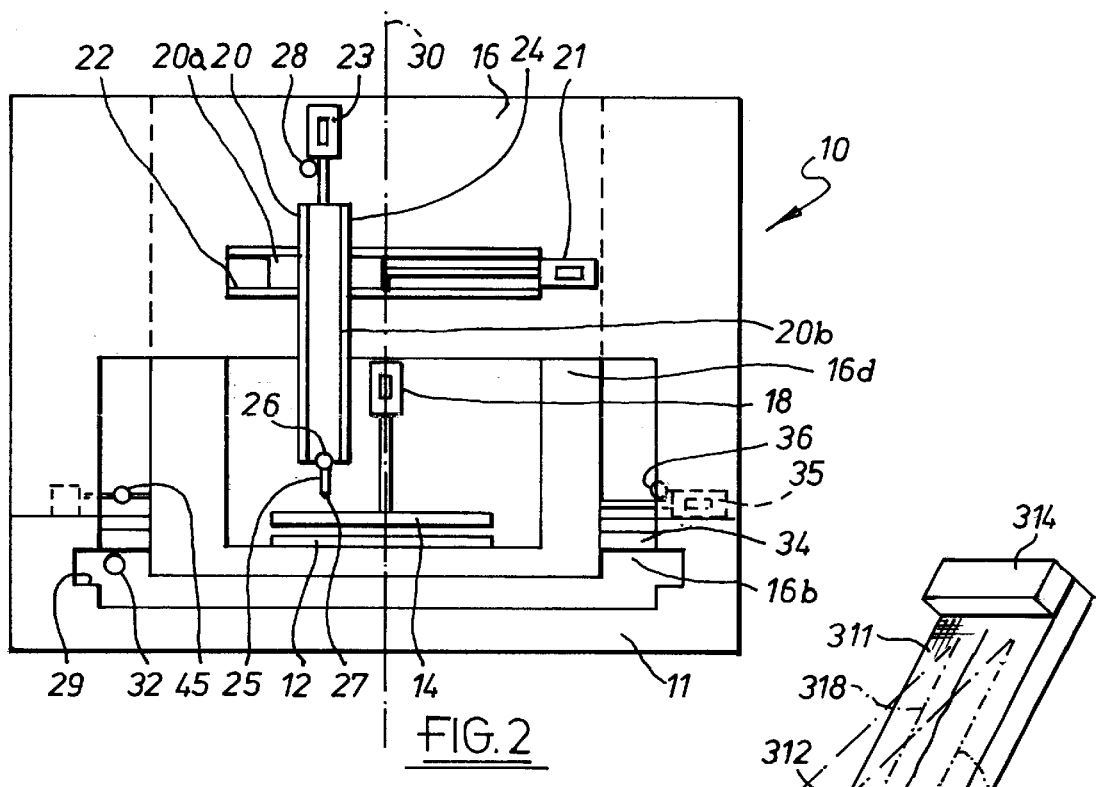
FIG.2
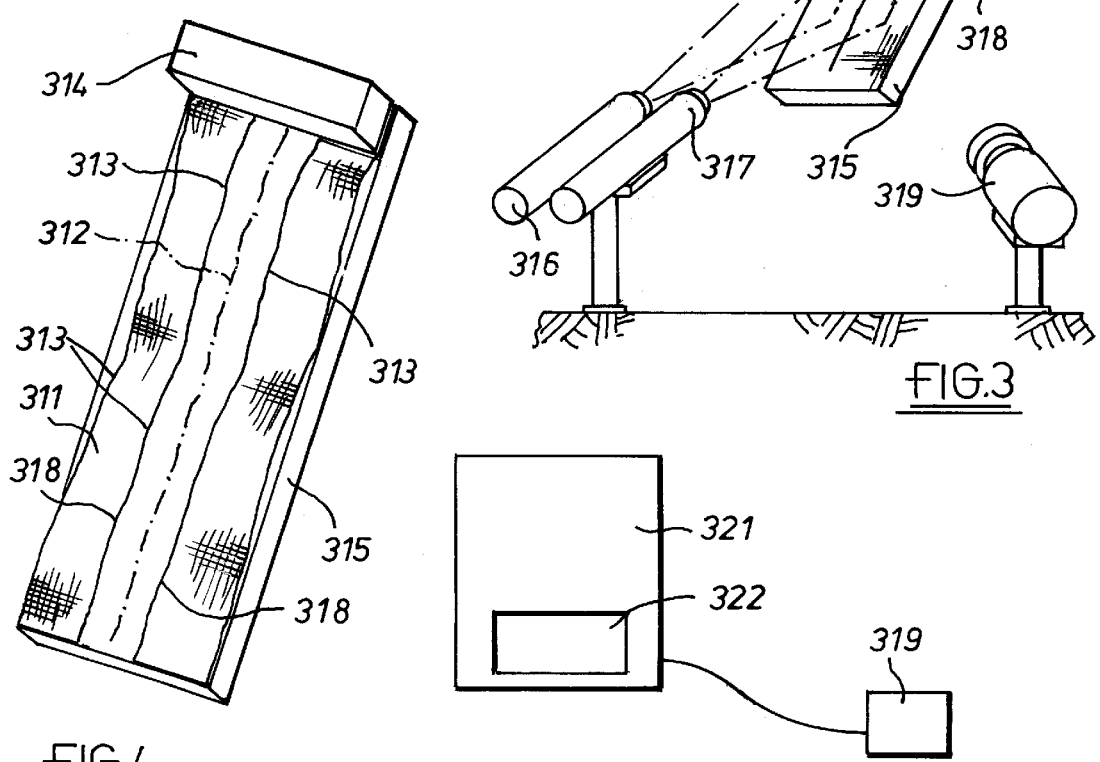
FIG.3
FIG.4
FIG.5

SHEET PARAMETER MEASUREMENT

This invention relates to the measurement of the mechanical properties of highly flexible or limp sheet material, for example paper, textile material, plastics and composite materials. In particular, the invention relates to the measurement of the tensile, shear, buckling, and compression strengths, sheet thickness, bending stiffness and surface qualities such as friction and roughness. The purpose of such testing, under normal loading without destruction of the sample of the material under test, is to determine the performance of the material in use, e.g. clothing fabrics during normal wear.

BACKGROUND OF THE INVENTION

To date, such measurements have generally been made independently on different samples of the material to be tested. For example, there is the widely accepted Kawabata Evaluation System for Fabric (KESF) for textile fabrics. With this system, different samples of the fabric to be tested are required to be placed in several different devices in order to make the measurements of the various properties listed above. One sample of the fabric to be tested is placed in a device which measures tensile and shear properties by clamping the sample at two spaced locations and moving the clamps apart and laterally relative to each other. This device has to be calibrated for each measurement on a sample. Bending strength, but not buckling, is measured by placing a different sample of the fabric in a second device. In this device the sample is mounted vertically and the device is very difficult to set up in trying to achieve an even tension in the fabric. One clamp makes a circumferential movement in order to measure the bending strength. Thickness measurement requires another measuring device. In this case a head moves vertically relative to the fabric in order to measure the thickness of the material and then its compressibility. For surface properties, a further sample of the material is clamped under load in a further device in which a head lowers and the material is then moved laterally relative to the head. Different probes on the head measure surface roughness and friction. It is very expensive to have all of these devices and very time consuming to place the different samples in the different devices in order to make all of the measurements. Another system is the Fabric Assurance by Simple Testing (FAST) system.

This is a simplified version of the KESF system, but at least two different samples are needed.

Thickness and compression are measured in one device at two positions of a movable head.

Bending is measured in another device in which the fabric is laid on a bed and is traversed by a moving plate on top of the fabric until the fabric extends over the edge of the bed and cuts a light beam. For tensile strength, the fabric is placed between two clamps in a further device, the lower one of the clamps being on an arm which is pivoted and has a weight on the other end. When the arm is released, the device registers the load in the fabric. The results from these tests are limited to the measured loads only and cannot provide full stress/strain profiles of the test samples. In addition the results from the two test systems are not very reproducible, due to the need for different sample sizes and the manual handling for each test. In the cosmetics and medical fields it is desirable to determine the effect cosmetic or medical creams and the like have on the human skin. To this end a fabric which has similar characteristics to human or animal skin is treated with the cream and the mechanical properties of fabric are then measured. For such an application the KESF and FAST systems are considered too expensive and too complicated.

SUMMARY OF THE INVENTION

It is an object of the present invention to provide a single apparatus for the measurement of the mechanical properties of a single sample of a limp sheet material in order to reduce the equipment costs compared with that of the number of existing devices required. It is also an object of the present invention to reduce the time and complexity of making such measurements and to increase the accuracy and reproducibility of such measurements compared with the existing methods.

The invention provides a device for the measurement of the mechanical properties of a limp sheet material, comprising a base, a pair of clamping members operable to clamp the sheet material to the base at spaced locations, load sensing means on at least one clamping member, at least one of the clamping members being movable away from and towards the other in the plane of the sheet material and laterally of the other in said plane, and a head assembly having a sensing device spaced from the base and movable theretowards and laterally of the plane of the sheet material.

One clamping member may be the at least one movable clamping member and the load sensing means may be mounted on the other clamping member. Two load sensing means having differing ranges of measurement may be mounted on the one clamping member, the first load sensing means being adapted to measure tensile load and the second load sensing means being adapted to measure buckling load. The measurement device may comprise a third load sensing means adapted to measure shear loads. The sensing device may comprise a further load sensing means and a surface characteristics sensing means.

Preferably the base is a plate which is disposed substantially horizontally, in which case the clamping members may be disposed above the base plate and positionally adjustable to clamp the sheet material. The measuring device may comprise position indicating means adapted to indicate the position of the at least one movable clamping member relative to a datum position. The at least one movable clamping member may be mounted on low friction slideways, and the slideways may be disposed remote from the axes of movement of the at least one movable clamping member. The head assembly may be disposed between the clamping members, and may be mounted on the base plate. The head assembly may comprise a slide part on which the sensing device is mounted for movement towards the base plate and, together with the slide part, laterally of the sheet material.

The base plate may have an edge to a side of the at least one movable clamping member remote from the other clamping member, over which edge the sheet material may be moved to cantilever thereover. The measurement device may comprise a beam transmitting device and a beam sensing device operable to receive the transmitted beam and detect when the sheet material interrupts the beam. The beam may be directed from beneath and spaced from the edge of the base plate at an angle of between 30° and 60° to the horizontal.

Preferably the beam is directed at an angle of 41.5° to the horizontal. The base plate may be formed to have a shallow recess between the spaced locations to reduce the frictional contact between the sheet material and the base plate.

The measurement device may comprise control means operable to control the sequence of movement of the at least one movable clamping member and the sensing device. The control means may also be operable to render operable the first or second load sensing means for measuring tensile load or buckling load respectively dependent on the direction of movement from the datum position of the at least one movable clamping member. The control means may be operable to vary the length of time between successive movements of the at least one movable clamping member and the sensing device. The control means may also be operable to adjust the speed of movement of the at least one movable clamping member and the sensing device. The control means may comprise programmable means for the selection of the measurements to be made, the speed of movement of the at least one movable clamping member and the sensing device, and the timing of the movements.

The movement of the at least one movable clamping member and the sensing device may be effected by respective stepper motors. The clamping members may also be moved between respective sample material release positions and their clamping positions by respective stepper motors.

In another aspect, the invention relates to methods and apparatus for the assessment of seam pucker and other surface irregularities.

Assessment of surface irregularities, particularly seam pucker, is at present largely a subjective matter. Attempts to introduce objectivity into the assessment have, to date, not been so successful as the result is non-standard. The same is true for measurements, generally, of surface irregularities of which seam pucker is typical—with the exception, possibly, of microscopic surface roughness measurements, necessarily automated and standardized because of inaccessibility to the naked eye—surface irregularity is "judged" rather than objectively measured.

The invention provides an objective assessment for seam pucker and other, comparable surface irregularities.

The invention comprises a method for the assessment of seam pucker and other surface irregularities comprising directing at the surface a line beam from an illuminator, imaging the line on the surface formed by the line beam and analysing data of the image to produce an objective indication of the degree of irregularity of the surface.

Parallel line beams may be directed at the surface. For the assessment of seam pucker, the parallel line beams may be directed to form lines on the surface parallel to and either side of the seam, and at an angle from the plane perpendicular to the surface.

The illuminator may comprise a line beam laser.

The line on the surface may be imaged by a pixel image such as a CCD array camera.

The image may be analysed in a computer programmed with image analysis software. The result of analysing the image may be a display of a distribution of severity of deviation of the surface from flat.

The surface may be that of a limp material, such as a textile fabric, mounted on a flat support base. The base may, for the assessment, be inclined steeply with the material clamped uppermost and resting against the base below the clamping location.

For consistency of measurement the material is preferably the same size as the bed, so no additional irregularity is occasioned by edge effects. A sample for assessment may be cut to size using the bed as a template.

The invention also comprises surface irregularity assessment apparatus comprising a line beam illuminator;

a support arrangement for the surface under assessment such that the line beam illuminator is directed at the surface to illuminate a line thereon;

an imaging arrangement adapted to image the line illuminated on the surface, by the line beam illuminator; and analysis means adapted to receive image data to produce an objective indication of the degree of irregularity of the surface.

There may be one, two or more line beam illuminators casting parallel beams. Beams may be cast in different arrangements to provide further information.

The imaging arrangement may comprise a pixel imaging arrangement, and may comprise a CCD array.

The line illuminator may be a laser.

The analysis means may comprise a computer programmed with image analysis software.

BRIEF DESCRIPTION OF THE FIGURES

Embodiments of the invention will now be further described with references to the accompanying drawings in which:

FIG. 2 is a view on line 2—2 of FIG. 1,

FIG. 3 is a perspective view of an apparatus for measuring seam pucker, in simplified form;

FIG. 4 is a view of an illuminated sample in the apparatus of FIG. 3; and

FIG. 5 is a block diagram of the apparatus of FIG. 3.

DETAILED DESCRIPTION

Figure 1:
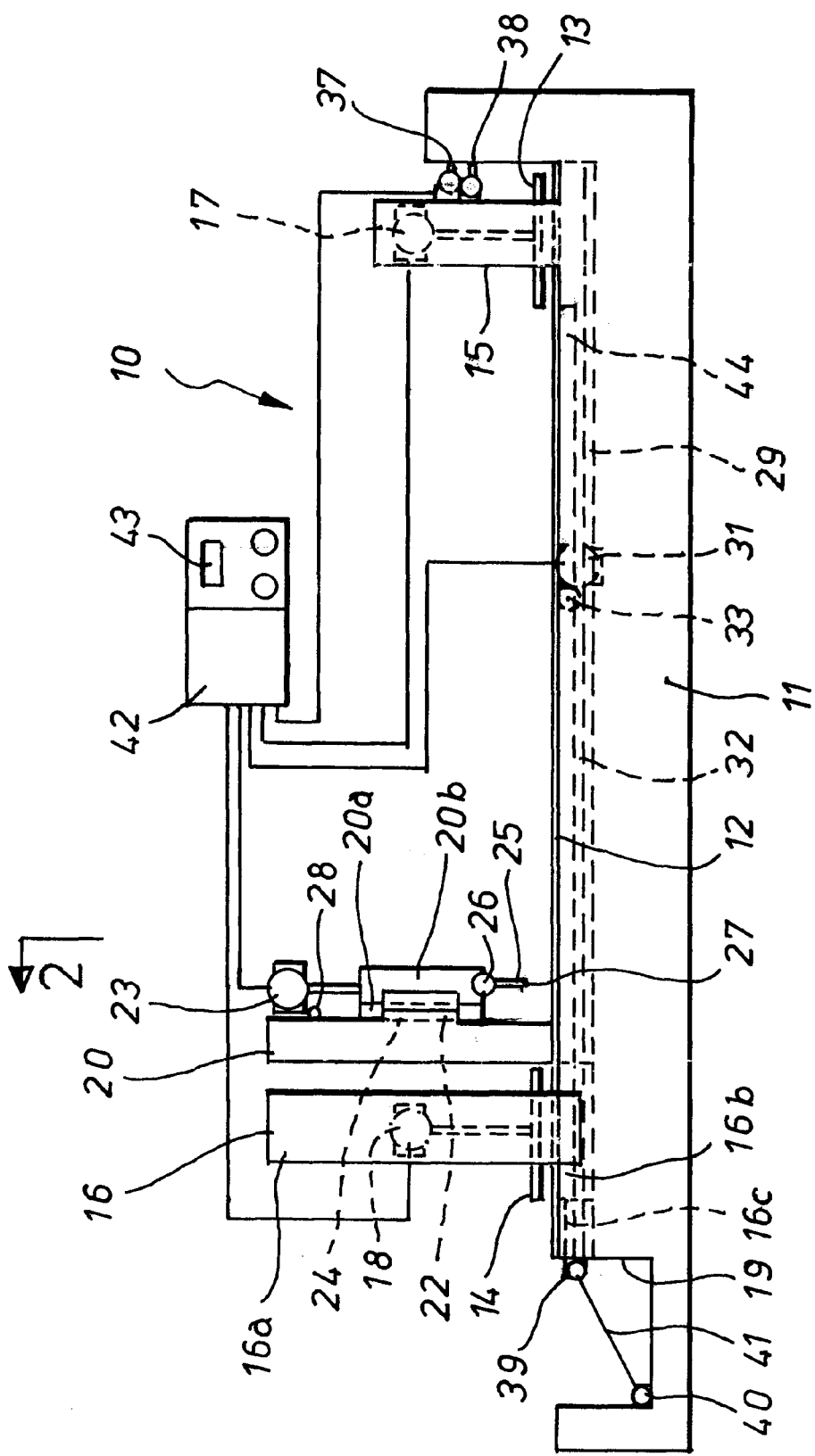
FIG. 1 is a front elevation.

Referring now to FIGS. 1 and 2, there is shown a measurement device 10 comprising a substantially horizontally disposed base plate 11 on which a sample 12 of the material to be tested is placed. A 'fixed' clamping member 13 and a 'movable' clamping member 14 are mounted on respective supports 15, 16 and are movable by respective stepper motors 17, 18 from their respective sample material release positions as shown downwardly towards the base plate 11 to clamp the sample 12. At this initial stage the 'movable' clamping member 14 and its 'movable' support 16 are in the 'datum position and the end of the sample 12 is aligned with the end 19 of the base plate 11. Mounted on a head support 20 is a head assembly comprising a slide part 20a which is movable by means of stepper motor 21 and lead screw laterally of the sample 12 in slideways 22 and a sensing part 20b which is movable by means of a stepper motor 23 vertically in slideways 24. The sensing part 20b has a sensing device 25 which incorporates load sensing means 26 and a surface characteristics sensing means 27. A position sensor 28 is provided on the support 20 to measure the height of the head assembly 20 relative to the base plate 11.

The 'movable' support 16 is mounted on the base plate 11 in low friction slideways 29 disposed remote from the axis 30 of movement of the 'movable' support 16 to minimise the effects of friction on the operation and measurement sensitivity of the measurement device 10. The 'movable' support 16 is movable by means of stepper motor 31 and lead screw 32 away from and towards the 'fixed' support 15, and a position sensor 33 indicates the position of the 'movable' support 16 relative to a datum position. The upper part 16a of the 'movable' support 16 is movable in slideways 34 in lower part 16b by stepper motor 35 laterally of the base plate 11. A position sensor 36 indicates the lateral position of the 'movable' support 16 relative to a datum central position. In fact, the 'fixed' support 15 is also mounted on the slideways 29 and is movable from its datum position 16 under the effect of a change in the tension in the sample 12. Any such change in tension is detected by load cells 37, 38. The 'movable' support 16 may be extended as shown to support the sample 12 when it is moved towards the edge 19 of the base plate 12 for the bending test described below.

Located adjacent the edge 19 of the base plate 12 is a beam transmitting device 39 and a beam sensing device 40 operable to receive the transmitted beam 41 and detect when the sample 12 interrupts the beam 41. The beam transmitting device 39 is mounted at the edge 19 and the beam 41 is directed downwardly towards the base plate 11 at an angle of 41.5° to the horizontal.

A control device 42, including programmable means 43 is provided to control automatically the operation of the measuring device 10, which is as follows. The prepared sample 12 of the material to be tested is placed in the measuring device 10 on the base plate 11 so that the end of the sample aligns with the edge 19 of the base plate 11. The control device 42 is activated and the clamping members 13, 14 are lowered by their motors 17, 18 to clamp the sample 12. Load cell 37, having a range of measurement appropriate to the measurement of tension in the sample 12 is brought into operation by the control means 42 and the other load cell 38 is taken out of operation. The motor 31 is then operated to move the 'movable' support 16 from its datum position in a direction away from the 'fixed' support 15. This movement applies a tensile load to the sample 12, which is measured by the load cell 37. A shallow recess 44 in the base plate 11 under the sample 12 reduces the effect of friction between the sample 12 and the base plate 11. The distance moved by the 'movable' support 16 is measured by the position sensor 33, so that a 'load-extension' relationship for the sample 12 can be determined. The control means 42 reverses the motor 31 to return the 'movable' support 16 to its datum position. The load sensor 37 is taken out of operation and the load cell 38, having a range of measurement appropriate to the measurement of buckling load in the sample 12, is brought into operation. Further movement of the 'movable' support 16 towards the 'fixed' support 15 enables the load in the sample 12 as it buckles to be measured by the load cell 38. The 'movable support 16 is then again returned to its datum position.

The sensing part 20b of the head support 20 is then lowered by means of the motor 23 until contact between the sample 12 and the surface characteristics sensing means 27. The height of the surface characteristics sensing means 27 above the base plate 11 is indicated by the position sensor 28 so as to determine the thickness of the sample 12. Further lowering of the sensing part 20b will apply a compressive load to the sample 12, as determined by the load cell 26. Correlation of the readings of the load cell 26 and the position sensor 28 will provide a 'Load-compression' relationship for the sample 12. The sensing part 20b is then raised to the position of contact between the sample 12 and the surface characteristics sensing means 27. Lateral movement of the slide part 20a along slideways 22 by means of motor 21 causes the surface characteristics sensing means 27 to measure the friction between it and the sample 12 and also the surface roughness of the sample 12. The sensing part 20b is then raised to its original position.

The control means 42 then activates motor 36 to move the upper part 16a of the 'movable' support 16 laterally of the base plate 11. This induces a shear in the sample 12, and the shear load is indicated by a further load cell 45. Correlation of the readings of the load cell 45 and the position sensor 36 will provide a 'Load-shear' relationship for the sample 12.

To determine the bending characteristics of the sample 12, the control means 42 now activates motors 17 and 18 to raise the 'fixed' and 'movable' clamping members 13, 14 to release the sample 12. Motor 31 is then activated to move the 'movable' support 16 and the sample 12 away from the 'fixed' support 15. During this movement the sample 12 is supported by the extended support 16c. This causes the end of the sample 12 to cantilever over the edge 19 of the base plate 11, eventually to bend and hang downwardly 50 as to interrupt the beam 41. The position sensor 33 indicates the amount of sample 12 extending over the edge 19 of the base plate 11 when the beam 41 is interrupted, this amount being dependent on the stiffness of the material of the sample 12.

If not all of the above measurements are required, suitable programming of the programmable means 43 can cause the control means 42 only to activate the relevant motors for the measuring device to perform the required operations. Furthermore, if the effect of the speed of application of any load to the sample 12 is required, the programmable means 43 can be programmed to alter the speed of operation of the relevant motor or motors. As a further benefit of the measuring device 10, cyclic loading of the sample 12 may be effected by suitable programming of the programmable means 43.

Alternative embodiments of measuring device according to the invention will be apparent to persons skilled in the art. For example, as an alternative to stepper motors, the movements of the movable parts of the measurement device may be effected by pneumatic or hydraulic cylinders or by linear motors. As another alternative construction, the slide and sensing parts 20a, 20b may be mounted on the upper part 16a of the 'movable' support 16. By means of the present invention measurements of tensile, shear, buckling, and compression strengths, sheet thickness, bending stiffness and surface qualities such as friction and roughness can be made on a single sample of a limp sheet material in a single measuring device, thereby reducing the time involved in performing the tests and the initial cost of purchasing the necessary equipment.

FIGS. 3 to 5 of the drawings illustrate a fabric sample 311 with a seam 312 giving rise to seam pucker—undulations 13 in the fabric either side of the seam 312—held by a clamp 314 on a support base 315 inclined steeply so the fabric rests on the base rather than hangs freely, but otherwise without any constriction that would give rise to specious undulation or flattening and of any pucker that might be present. A bridge 315a on the support base 315 restricts movement of the sample 311 during monitoring.

The base 315 is removable from an enclosure in which the assessment is carried out and may be used as a template in cutting a sample for assessment from a larger piece.

Two parallel line beam lasers 316, 317 are directed at the sample 311 so that they illuminate lines 318 either side of the seam 312.

As seen in FIG. 4, these lines take on a undulating appearance because of the seam pucker. The sample is imaged by a CCD camera 319, which is arranged at such a distance from the sample that the distortions due to seam pucker in the lines 318 are visible in the image.

The whole is enclosed, for the assessment, in a box, and should, to prevent laser light escaping that might damage eyes be viewed directly, there being an interlock arrangement to ensure the lasers cannot operate unless the box is closed.

The image from the camera 319 is fed to a computer 321, FIG. 5, with a vision card 322 and software capable of analysing the image by suitable routines to assess the degree and spatial frequency of any undulation caused by seam pucker.

Clearly a similar set-up can be employed to assess other types of surface irregularity.

The apparatus may readily be miniaturized and presented as a hand-held arrangement for portable use.

What is claimed is:

1. A device for the measurement of at least two mechanical properties of a limp sheet material, the measurements being selected from the group consisting of tensile strength, surface properties, buckling load, shear load, and load/compression measurement, the device comprising a base, a pair of clamping members operable to clamp the sheet material to the base at spaced locations, load sensing means on at least one clamping member, at least one of the clamping members being movable away from and towards the other in the plane of the sheet material and laterally of the other in said plane, and a head assembly having a sensing device adapted for at least two of said measurements by being spaced from the base and movable there towards and laterally of the plane of the sheet material.

2. A measurement device according to claim 1, wherein one clamping member is the at least one movable clamping member and the load sensing means is mounted on the other clamping member.

3. A measurement device according to claim 2, wherein two load sensing means having differing ranges of measurement are mounted on the other clamping member.

4. A measurement device according to claim 3, wherein a first one of the load sensing means is adapted to measure tensile load and a second one of the load sensing means is adapted to measure buckling load.

5. A measurement device according to claim 4, comprising a third load sensing means adapted to measure shear loads.

6. A measurement device according to claim 1, wherein the sensing device comprises a further load sensing means and a surface characteristics sensing means.

7. A measurement device according to claim 1, wherein the base is a plate which is disposed substantially horizontally.

8. A measurement device according to claim 7, wherein the clamping members are disposed above the base plate and are positionally adjustable to clamp the sheet material.

9. A measurement device according to claim 7, wherein the base plate has an edge to a side of the at least one movable clamping member remote from the other clamping member, over which edge the sheet material may be moved to overhang therefrom.

10. A measurement device according to claim 9, comprising a beam transmitting device and a beam sensing device operable to receive the transmitted beam and detect when the sheet material interrupts the beam.

11. A measurement device according to claim 10, wherein the beam is directed from the beam transmitting device adjacent the edge of the base plate at an angle of between 30° and 60° to the horizontal.

12. A measurement device according to claim 11, wherein the beam is directed at an angle of 41.5° to the horizontal.

13. A measurement device according to claim 7, wherein the base plate is formed to have a shallow recess between the spaced locations to reduce the frictional contact between the sheet material and the base plate.

14. A measurement device according to claim 1, comprising positioning indicating means adapted to indicate the position of the at least one movable clamping member relative to a datum position.

15. A measurement device according to claim 14, wherein the at least one movable clamping member is mounted on low friction slideways.

16. A measurement device according to claim 1, wherein the slideways are disposed remote from the axes of movement of the at least one movable clamping member.

17. A measurement device according to claim 1, wherein the head assembly is disposed between the clamping members.

18. A measurement device according to claim 17, wherein the head assembly is mounted on the base plate.

19. A measurement device according to claim 18, wherein the head assembly comprises a slide on which the sensing device is mounted for movement towards the base plate and laterally of the sheet material.

20. A measurement device according to claim 1, comprising control means operable to control the sequence of movement of the at least one movable clamping member and the sensing device.

21. A measurement device according to claim 20, wherein the control means is operable to render operable the first or second load sensing means for measuring tensile load or buckling load respectively dependent on the direction of movement from the datum position of the at least one movable clamping member.

22. A measurement device according to claim 20, wherein the control means is operable to vary the length of time between successive movements of the at least one movable clamping member and the sensing device.

23. A measurement device according to claim 20, wherein the control means is operable to adjust the speed of movement of the at least one movable clamping member and the sensing device.

24. A measurement device according to claim 23, wherein the control means comprises programmable means for the selection of the measurements to be made, the speed of movement of the at least one movable clamping member and the sensing device, and the timing of the movements.

25. A measurement device according to claim 1, wherein the movement of the at least one movable clamping member and the sensing device is effected by respective stepper motors.

26. A measurement device according to claim 25, wherein the clamping members are moved between respective sample material release positions and their clamping positions by respective stepper motors.

* * * * *